US00RE40456E

(19) United States
(12) Reissued Patent
Bates

(10) Patent Number: US RE40,456 E
(45) Date of Reissued Patent: Aug. 12, 2008

(54) ACOUSTIC WAVE IMAGING APPARATUS AND METHOD

(76) Inventor: Kenneth N. Bates, 15580 SW. Burntwood Ct., Beaverton, OR (US) 97007

(21) Appl. No.: 09/628,942

(22) Filed: Jul. 28, 2000

Related U.S. Patent Documents

Reissue of:
(64) Patent No.: 5,787,049
Issued: Jul. 28, 1998
Appl. No.: 08/554,859
Filed: Nov. 7, 1995

(51) Int. Cl.
*G03B 42/06* (2006.01)
*G01N 29/00* (2006.01)

(52) U.S. Cl. ..... 367/7; 367/103; 367/105; 73/625; 73/626

(58) Field of Classification Search ..... 73/625, 73/626; 128/661.01, 662.06; 367/7, 137, 367/103, 105
See application file for complete search history.

(56) References Cited

U.S. PATENT DOCUMENTS 3,953,825 A * 4/1976 Kino et al. ..... 73/626
4,127,034 A * 11/1978 Lederman et al. ..... 73/626
4,140,022 A * 2/1979 Maslak ..... 73/626
4,155,258 A * 5/1979 Engeler et al. ..... 73/626
4,155,259 A * 5/1979 Engeler ..... 73/626
4,155,260 A * 5/1979 Engeler et al. ..... 73/626
4,271,707 A * 6/1981 Lakin ..... 73/614
4,550,606 A * 11/1985 Drost ..... 73/626
4,974,211 A * 11/1990 Corl ..... 367/7
5,014,712 A * 5/1991 O'Donnell ..... 128/661.01
5,016,018 A * 5/1991 Chang et al. ..... 342/351
5,058,593 A * 10/1991 Forestieri et al. ..... 128/661.07
5,622,177 A * 4/1997 Breimesser et al. .... 128/662.06

OTHER PUBLICATIONS

Bates, K.N., "A Highly Electrostrictive Ceramic", 1997 Ultrasonics Symposium Proceedings, IEEE Cat # 77CH1264–ISU, pp. 393–396.*

Bates and Wang, PEOATS and ESOATS, date unknown, Chirp Focused Transmitter Theory, J. Souquet et al., Stanford University.*

* cited by examiner

*Primary Examiner*—Ian J. Lobo
(74) *Attorney, Agent, or Firm*—Steven J. Adamson

(57) ABSTRACT

An acoustic imaging apparatus and method that achieves desired delays with coded signals. Linear, curved linear and sector scanning is provided in 1-D arrays and planar, curved planar and sector scanning is provided in 2-D arrays. Composite and non-linear implementations are presented. Dynamic and discrete dynamic focusing is disclosed for the relevant arrays. The 2-D array makes possible 3-D imaging.

40 Claims, 9 Drawing Sheets

Fig. 6B
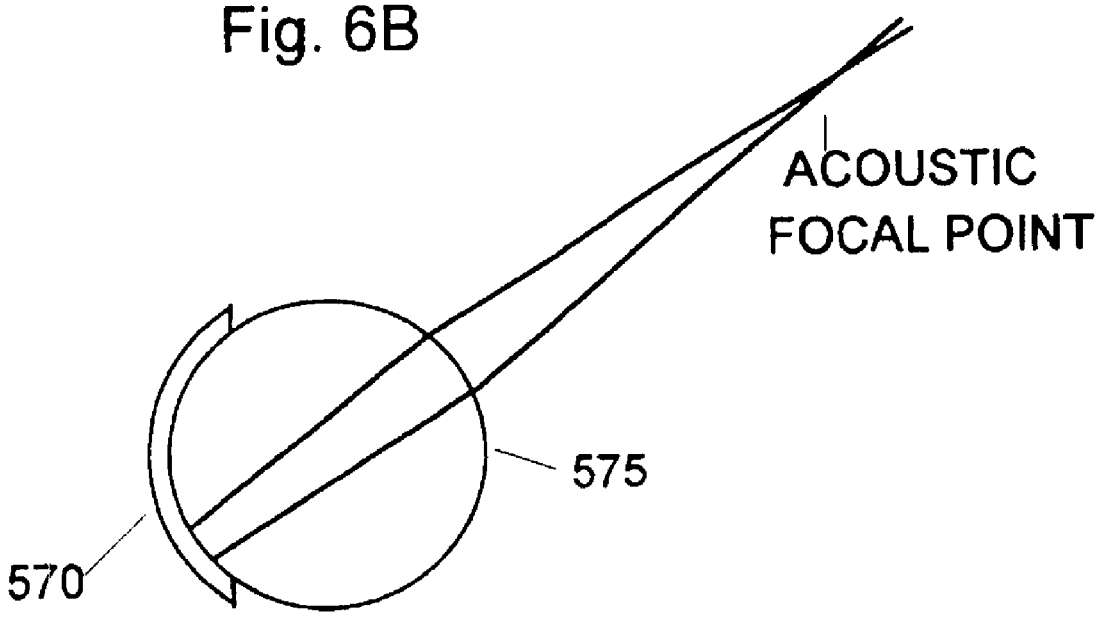
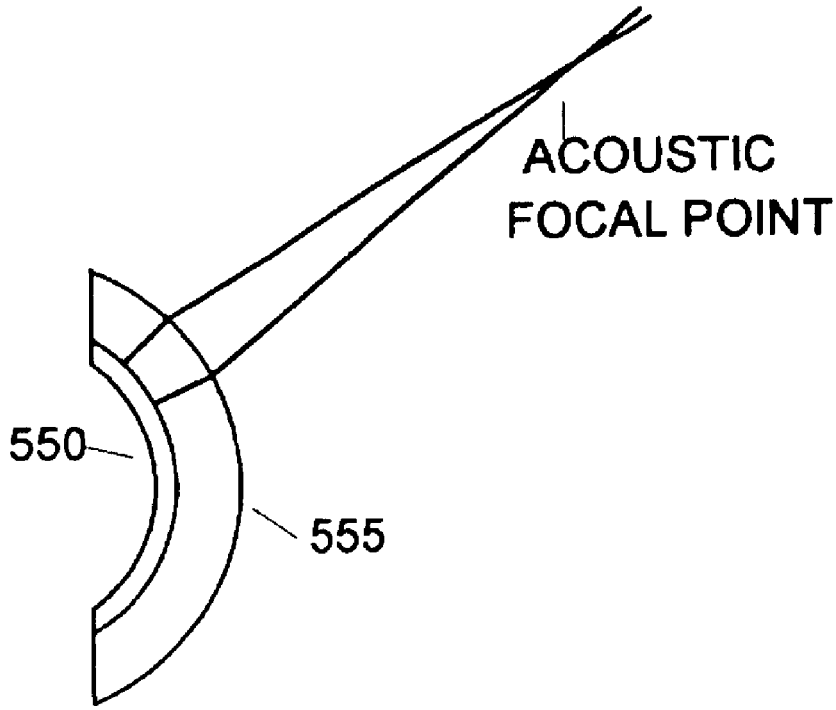
Fig 6A

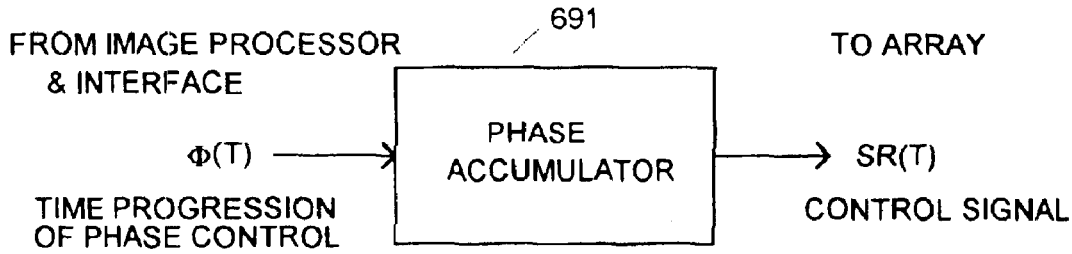
Fig. 10
Fig. 9
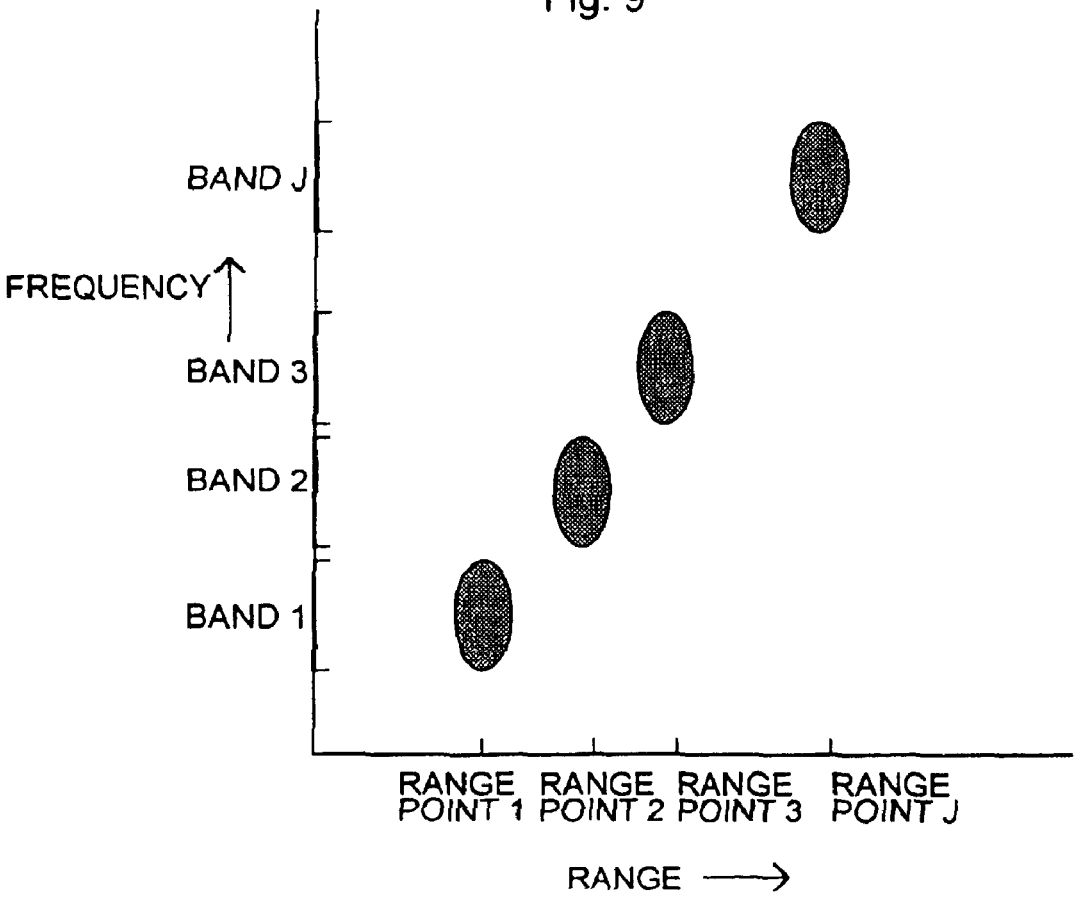

ACOUSTIC WAVE IMAGING APPARATUS AND METHOD

Matter enclosed in heavy brackets [ ] appears in the original patent but forms no part of this reissue specification; matter printed in italics indicates the additions made by reissue.

FIELD OF THE INVENTION

The present invention relates to acoustic wave imaging systems.

BACKGROUND OF THE INVENTION

Conventional acoustic wave imaging systems use a one dimensional (1-D) array of electro-acoustic transducers, for example, a 1×100 array, and have been configured to achieve linear, curved linear and sector scanning. Coherence in the transmission and receipt of acoustic signals is achieved by the utilization of delay devices in the signal processing channels. Present one dimensional systems are disadvantageous due to (1) the manner in which they are constructed and (2) inherent limitations in their scanning capabilities. With respect to the manner in which they are constructed, one disadvantage is that the use of delay elements[,] and related electronics adds considerably to the cost of one dimensional systems. With respect to inherent limitations, one dimensional scanning systems are disadvantageous in that they only provide two dimensional images.

To increase diagnostic capabilities it is desirous to have an acoustic imaging system that scans in two dimensions and thus produces a 3-D image. A problem with applying current 1-D technology to 2-D array imaging is that a vast number of electrical connections and processing electronics are required to serve an array of practical size. For example, a 100×100 array would have 10,000 individual transducers. Standard technology would require 10,000 electrical connections and processing channels. At an approximate cost of $100 per channel, such a system would require an outlay of $1M merely for channel electronics. In addition, if per channel power consumption is approximately 0.1 watt, then the system power requirement becomes at least 1 KW.

As a result of the disadvantageous aspects of providing large numbers of processing channels, current research efforts are directed towards achieving high performance with fewer array elements. Two prior art approaches are (1) the use of a two dimensional array with a reduced number of columns, termed a 1.5-D array, and (2) a thinned 2-D array.

A typical embodiment of a 1.5-D array is a 100 row×3–5 column array. Due to reduced aperture, 1.5-D arrays may not offer the increase in elevation resolution that will justify their added expense and complexity. Furthermore, research has shown that the use of aberration correction with 1.5-D arrays may not improve the image quality over that obtained using correction with a 1-D array.

In a thinned array, the number of array elements and associated electronics is reduced to several hundred by judiciously using only a selected number of transducers throughout the array aperture. This approach, however, has lead to significantly higher sidelobes in the beam profile of the system, compared to sidelobes in a beam profile for a full 2-D array. Thus, these systems are not suitable for such common uses as medical diagnostic imaging and the like which requires low and extremely low level sidelobes.

It should also be noted that the prior art does include 2-D annular arrays. These arrays are formed of concentric annual rings. They produce only a single ray, and while they perform dynamic focusing, they do not provide sector scanning. Scanning is achieved by physically moving the arrays.

In view of the foregoing, it should be apparent that a need exists in the art for both (1) a more economically constructed one dimensional scanning system, and (2) an acoustic wave imaging system that provides the high degree of resolution achievable with a full 2-D array, while reducing the number of processing channels and other circuitry associated therewith, amongst other needs.

SUMMARY OF THE INVENTION

Accordingly, it is the object of the present invention to provide an acoustic imaging system having a 1-D array that uses coded signals to achieve requisite delays.

It is another object of the present invention to provide an acoustic imaging system having a 2-D array that has a number of processing channels that is less than the number of transducers.

It is another object of the present invention to provide a multiplicity of embodiments and implementations for these 1-D and 2-D acoustic arrays.

*It is also an object of the present invention to transmit and/or receive acoustic energy with these 1-D or 2-D acoustic arrays.*

These and related [objective] *objectives* of the present invention are achieved by use of the acoustic wave imaging system and method described herein.

Amongst other aspects, the present invention discloses a manner of using coded signals to achieve desired delays in 1-D, 2-D and annular array imaging systems. For 1-D imaging array systems, a manner of making and practicing linear, curved linear and sector scanning arrays that are low cost and potentially portable is presented. This teaching also applies to annular arrays. For 2-D array imaging systems, a manner of making and practicing these systems for rapid 3-D volume images and/or real time, arbitrary scan plane, 2-D sector, planar, or curved planar images is presented. In addition, the 2-D array taught herein allows for the implementation of multi-dimensional aberration correction which may allow ultrasonic images to approach the image acuity of MRI and X-ray CAT imaging systems, and to do so at a fraction of the cost of these imaging modalities.

Both dynamic focusing and discrete dynamic focusing is taught for the systems herein. Composite and non-linear implementations, as defined herein, are also disclosed.

In one embodiment, the present invention comprises a plurality of electro-acoustic [transducer] *transducers*, each capable of generating an electrical signal indicative of an incident acoustic wave; means in communication with each [transducers] *transducer* for generating a coded signal for transmission by each of said transducers; and means in communication with each of said transducers for modifying a coded signal received by the transducers to achieve a desired delay.

The present invention also comprises a plurality of electro-acoustic transducers, each capable of generating an electrical signal indicative of an incident acoustic wave and arranged in an array; control means in communication with each of said transducers and having a plurality of control channels for controlling said transducers; and means in communication with each of said transducers for processing image data therefrom; wherein said plurality of control channels is fewer in number than said plurality of transducers.

The invention also includes an transducer element comprised of non-linear electro-acoustic, non-linear dielectric material.

And in yet another of many embodiments, the present invention includes an array of electro-acoustic transducers having a plurality of rows and columns; a plurality of row control lines, each of which is coupled to the transducers in one of said plurality of rows; a plurality of column control lines, each of which is coupled to the transducers in one of said plurality of columns; and control means coupled to each of said plurality of row and column control lines for generating a control signal for each [transducers] *transducer* that is a combination of control signals on the row and column control lines for that transducer.

Methods for realizing a desired delay and for achieving planar, curved planar and sector scanning are also disclosed.

The attainment of the foregoing and related advantages and features of the invention should be more readily apparent to those skilled in the art, after review of the following more detailed description of the invention taken together with the drawings.

BRIEF DESCRIPTION OF THE DRAWINGS

FIGS. 6a–6b are diagrams of curved planar arrays in accordance with the present invention.

FIG. 9 is a range point versus frequency band diagram in accordance with the present invention.

FIG. 10 is a block diagram of a phase accumulator in accordance with the present invention.

DETAILED DESCRIPTION

The present invention includes both 1-D and 2-D array acoustic imaging systems. Both of these systems may be realized in a multiplicity of embodiments and may be implemented in different material.

For the 2-D array scanning system at least 3 practical embodiments are contemplated. They are the planar array, the curved planar array, and the sector scanning embodiments. At least two different implementations are also contemplated. They are the composite electronic/acoustic implementation (hereinafter referred to as the "composite" implementation) and the non-linear electro-acoustic, non-linear dielectric implementation (hereafter referred to as the "non-linear" implementation. One difference between the composite and non-linear implementations is that a mixing function (taught below) is provided in an electronic circuit fabricated in semiconductor material in the composite implementation, while in the non-linear implementation, that same mixing function is achieved as a characteristic of the selected non-linear material. As will be described in more detail below, the planar and curved planar array can be achieved in both composite or non-linear implementations, while sector scanning is achievable in the composite implementation.

The 1-D system is in large part a subset of the 2-D system and hence, linear scanning, curved linear scanning, and sector scanning may be realized. The teachings herein for the two different implementations of 2-D arrays applies likewise to 1-D arrays.

The 2-D and 1-D scanning systems are now presented in more detail. A general overview of a 2-D system is presented first in which a 1-D array may be substituted with apparent variation, followed by a description of system operation. Discussion of more specific embodiments is then provided, including both (i) achieving ranging in angular scanning and (ii) configuring a 1-D system, amongst other aspects.

Figure 1:
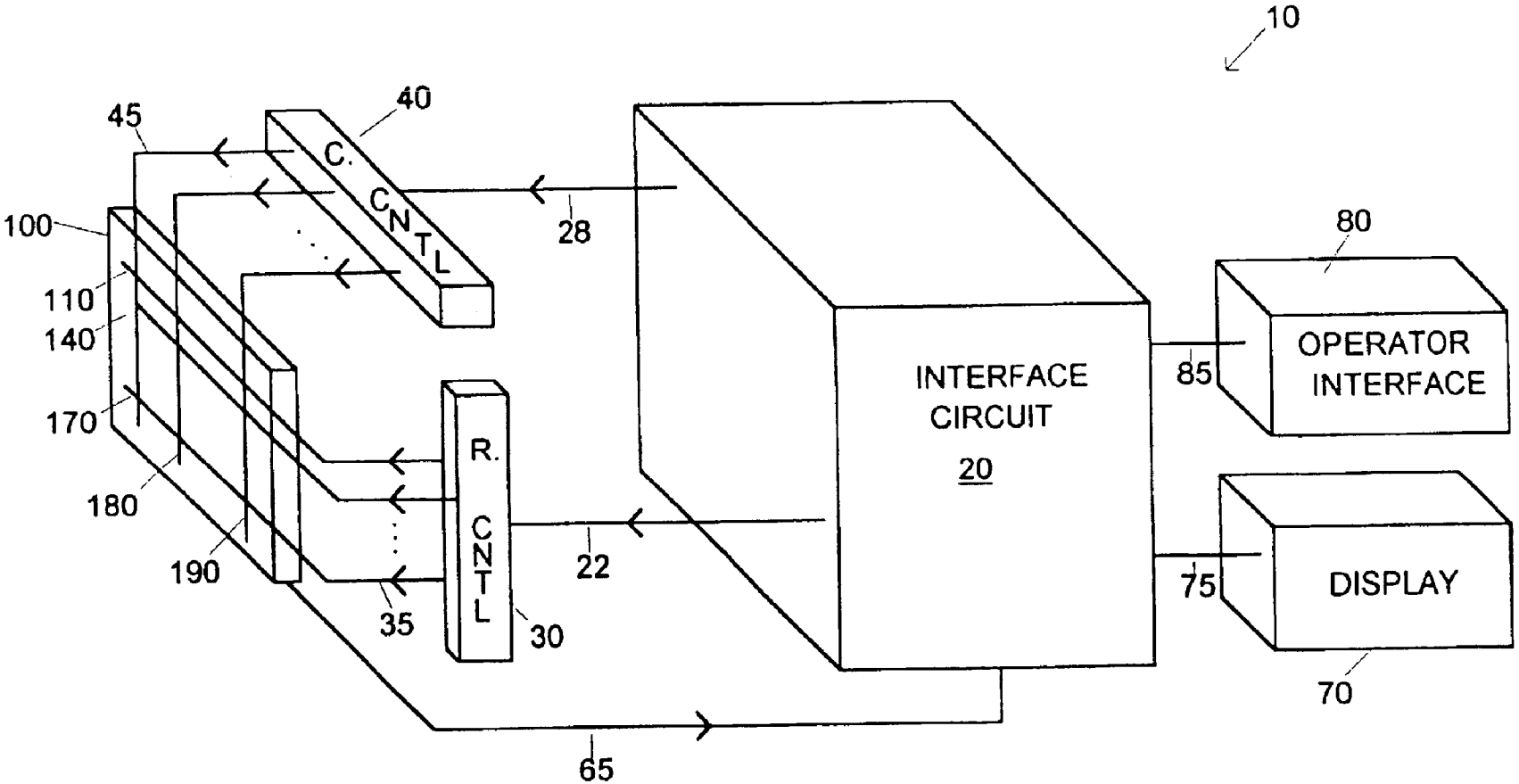
FIG. 1 is a perspective view of an acoustic wave imaging system in accordance with the present invention.

Referring to FIG. 1, a perspective view of an acoustic wave imaging system 10 in accordance with the present invention is shown. The system 10 includes interface circuit 20 which is connected via line 85 to operator interface componentry represented by reference numeral 80 and via line 75 to a display mechanism 70. Both the operator interface componentry 80 and the display mechanism 70 are known in the art and are discussed in more detail below with reference to FIG. 3. The interface circuit 20 is also connected, via line 22, to a row control circuit 30 and, via line 28, to a column control circuit 40. The row and column control circuits 30,40 control the phase and frequency of signals propagated to a plurality [a] *of* M rows and N columns in an array 100 of acoustic transducer elements. Each transducer element [comprises a acoustic transducer] (cells 110, [120,]140,170, 180,190 are indicated in FIG. 1) [and its] *includes a* corresponding transducer (shown in FIG. 2). The row control signals are propagated over M row control lines or processing channels, represented generally by arrow 35, and the column control signals are propagated over N column control lines or processing channels, represented generally by arrow 45.

Acoustic waves incident or transducers in array 100 cause the generation of a corresponding electrical signal that is combined with the row, X-axis, and column, Y-axis, control signals in each transducer cell and then combined with the output of all other cells before propagation over line 65 to interface circuit 20 in a manner discussed below. In interface circuit 20, the signal is processed for imaging and output via line 75 to display mechanism 70 for display. The interface circuit 20 is discussed in more detail below with reference to FIG. 3.

Figure 2:
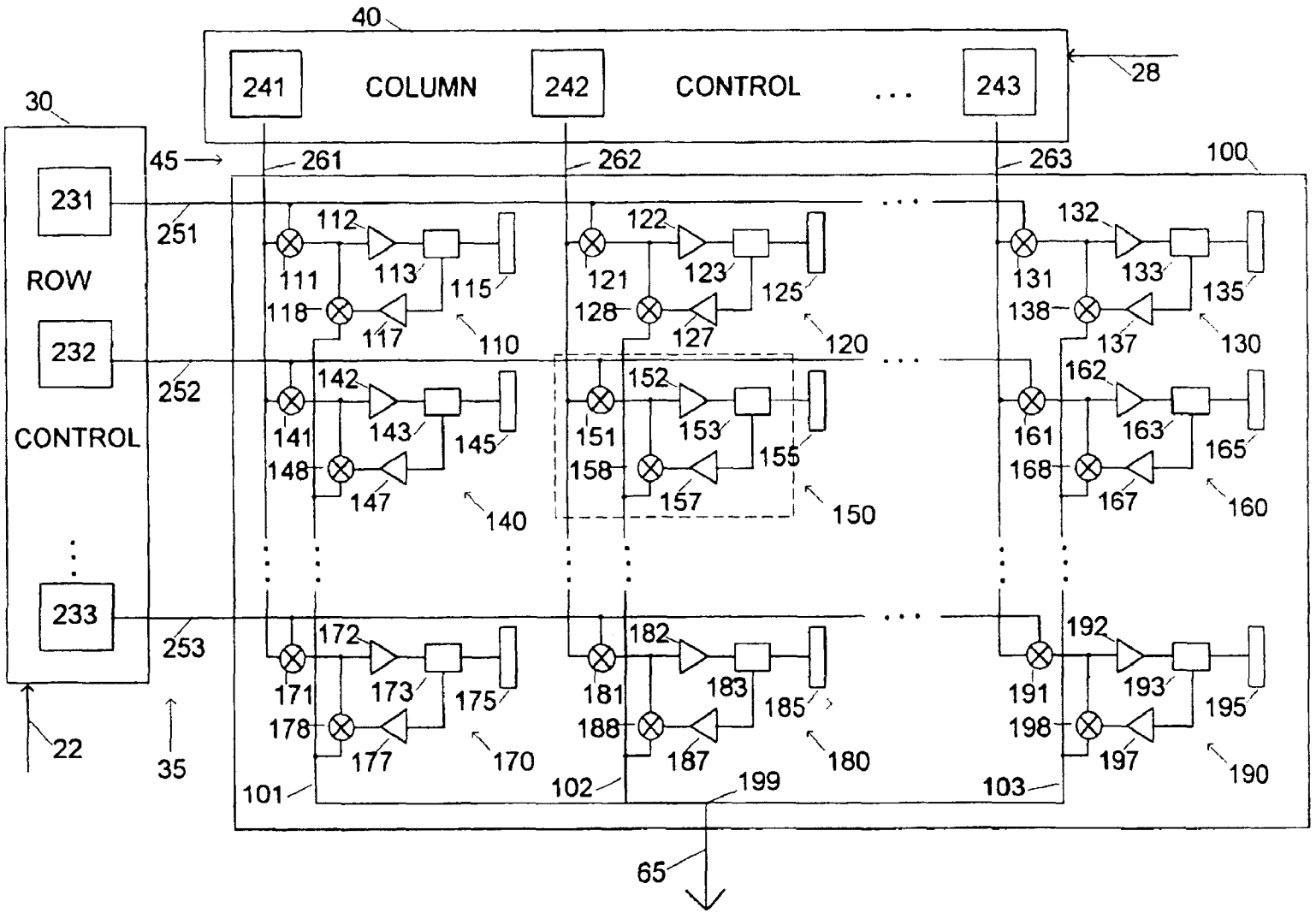
FIG. 2 is a schematic/block diagram of an acoustic transducer array and control circuits therefor in accordance with the present invention.

Referring to FIG. 2, a schematic/block diagram of array 100 and row and column control circuits 30 and 40, respectively, is shown (the array is presented as a schematic and the control circuits as block diagrams). The array is comprised of M rows and N columns and a transducer is preferably located proximate the intersection of each row and column signal line. Conventional 1-D arrays often contain 64 or 128 linearly arranged transducers. Accordingly, the array 100 is anticipated to have a size ranging from 64×64 to 128×128 transducers, and thus an approximate size of 100×100 is made reference to herein. In planar and curved planar scanning, discussed below, the array size may be much larger, for example 200×200 to 500×500 or a rectangular combination thereof, of which only a sub-unit is active at any given time. For example, the planar array may be 400×400 transducers, with a subaperture of 100×100 transducers that is active at a given time. If the embodiment of FIG. 2 has 100 row lines and 100 column lines, then 10,000 transducers are supported.

In the composite implementation the transducers are standard electro-acoustic transducers. They are processed to a particular size that affords an appropriate center frequency and bandwidth. In a preferred embodiment, those parameters are respectively 5 MHz and 4 MHz.

FIG. 2 illustrates 9 transducer cells 110 [(not labelled in FIG. 2 due to crowding in the figure, but labelled in FIG. 1)], 120,130,140,150,160,170,180,190 and their corresponding acoustic transducers *115*,125,135,145,155,165,[176]*175*, 185,195. In the composite implementation, each transducer is mounted to its corresponding cell in the same manner that transducers are connected to semiconductor substrates in IR focal plane arrays or the like. The dotted lines are provided to indicate that the number of cells is variable and may be modified in either dimension. Cell 150 is surrounded by a dashed line and will be described as a representative cell.

Cell 150 includes a first mixer 151 for mixing row and column control signals in a manner described below. This mixer is a standard high quality electronic mixer and is preferably doubly balanced. The output of mixer 151 is input to a transmit amplifier (hereinafter referred to as "buffer") 152 which in turn is connected to a transmit and receive (T/R) switch 153. The T/R switch 153 is controlled by interface circuit 20 (connection not shown, but known in art) and is connected to both the electro-acoustic transducer 155 and an amplifier 157. When an acoustic wave is received at transducer 155, a corresponding signal is propagated through T/R switch 153 to amplifier 157. The output of amplifier 157 is connected to a second mixer 158 which combines the corresponding signal with the output of first mixer 151. The output of second mixer 158 is connected to the output of the second mixers 128,188 from each of the other cells 120,180 in the same column via line 102. The combined second mixer output signals from each column (line 101 provides the combined second mixer signal for mixers 118,148,178 and line 103 provides the combined second mixer signal from mixers 138,168,198) are connected at point 199 and transmitted to interface circuit 20 (FIG. 1) on signal line 65.

The components of cell 150 are provided in the other cells and are identified therein by both a similar geometric symbol and reference numerals that use the same number in the units digit. For example, the first mixer 151 of cell 150 is identified as 111 in cell 110, 121 in cell 120, etc. It should be noted that although a buffer, a T/R switch and an amplifier are provided in each cell to improve signal characteristics, their use is not required to achieve the mathematical signal processing described herein.

The row control circuit 30 consists of a plurality of individual row signal generating circuits 231. A first of these [in] *is* connected via line 251 to the first mixer of cells 110,120, 130. Similarly, a second and a last row signal generating circuit 231 are connected via lines 252 and 253 to cells 140, 150,160 and cells 170,180,190, respectively. The column control circuit 40 consists of a plurality of individual column signal generating circuits 241. A first of these [in] *is* connected via line 261 to the first mixer of cells 110,140, 170. A second and a last column signal generating circuit 241 are connected via lines 262 and 263 to cells 120,150,180 and cells 130,160,190, respectively.

The row and column control are connected to the system control circuitry 300 (of FIG. 3) and provide frequency and phase modified signals in accordance with equations below, e.g., chirps on transmit, continuous waves during receive, and multiple component large bandwidth signals for sector scanning range focusing. In one embodiment, the row and column control circuits 30, 40 include frequency generators and phase shifters which are generally known in art and which receive initial values and control signals from interface circuit 20. Amplitude control may also be provided to improve signal processing and to correct for frequency dependent attenuation in the body.

Figure 3:
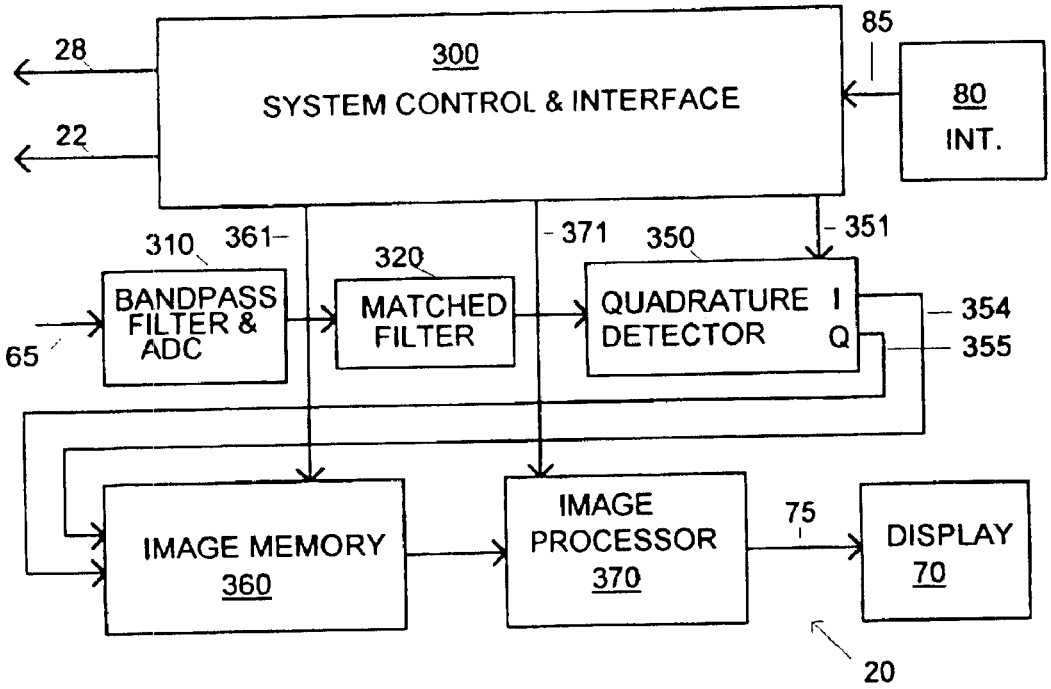
FIG. 3 is a block diagram of interface circuitry for an acoustic wave imaging system in accordance with the present invention.

Referring to FIG. 3, a block diagram of an interface circuit 20 in accordance with the present invention is shown. The interface circuit 20 includes system control circuitry, designated by block 300, that communicates over line 85 with the operator interface 80, over line 351 with a detector 350, over line 371 with an image processor 370, line 361 with image memory 360, and over lines 22 and 28 to the row and column control circuits (30,40 of FIG. 1). Operator interface 80 is generally known in the art and may include a key board and control knobs or the like for the entry of time, gain and control signals, patient data, transmit power, etc. Furthermore, circuitry and software for implementing the timing, signal generation, signal processing and related functions of the system control circuitry 300 is also generally known. It may include a system clock for synchronizing timing and other control signals, a microcontroller or equivalent discrete circuitry and related logic. Designing a program and logic to implement the equations herein would be apparent to one skilled in the art given the teachings herein.

The output signal from array 100 is propagated over line 65 to a filter 310 and preferably to an analog to digital converter (ADC), represented collectively as 310. This circuit may also include signal conditioning circuitry. In a preferred embodiment for broadband operation, a matched filter 320 (discussed below) is connected to the output of the bandpass filter/ADC 310 and the matched filter 320 is in turn connected to a detector 350. The detector 350 is provided to convert a signal output from the matched filter 320, which may potentially be 2–3 sinusoidal cycles, into a single unipolar pulse. A quadrature detector is preferred for Doppler processing.

Outputs from the detector 350 are propagated over line 354 and 355 to image memory 360 which in turn is connected to the image processor 370. Control signals from system control 300 are generated and propagated over lines 351,361,371 to detector 350, image memory 360, and image processor 370, respectively, in a generally known manner to result in the propagation of a display signal on line 75 to display mechanism 70. The display mechanism 70, may be a monitor, a projection screen, stereoscopic glasses, an image recording device, or any other display devices that is capable of displaying two or three dimensional images. Circuitry for implementing filter/converter 310, matched filter 320, detector 350, memory 360 and image processor 370 are generally known in the art. It should be recognized that while an ADC is preferred at 310, the same designated signal processing up until the image memory 360 may be performed with known analog circuitry.

In operation, data from detector 350 is stored in memory 360 in such a manner that it is read out by image processor 370 and propagated to display mechanism 70 in the same manner that data is propagated for a CRT, for example, in a 2-D imaging system, or stereoscopically for 3-D imaging.

Referring to FIGS. 1–3 collectively, acoustic signal focusing requires generation of a coherent wavefront during transmission mode and receipt of a coherent wavefront during receive mode. Such coherence is achieved by delaying the timing of transmit or receive signals an appropriate amount for a particular transducer based on its location in array 100. The delay is achieved through the use of coded signals. For purposes of the present invention, a coded signal is defined as any signal in which a change in a measurable characteristic thereof, e.g., frequency or phase, results in a change in time delay at a matched output therefor. One suitable coded signal is a linear FM chirp, which is taught herein in conjunction with a matched filter.

Figure 4:
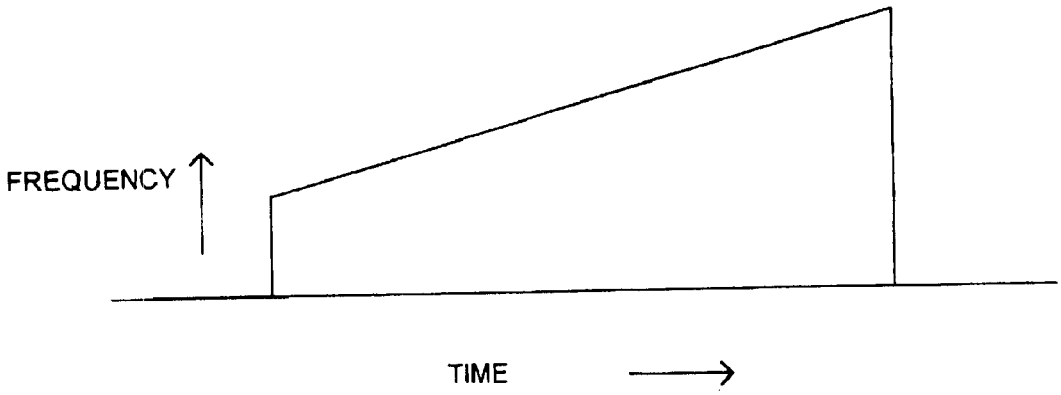
FIG. 4 is a diagram of a chirp signal.

Referring to FIG. 4, a frequency versus time diagram is shown for a linear FM chirp. Chirps as a characterized electrical signal and matched filters therefor are generally known. Though an up chirp is shown it should be recognized that since the attenuation of sound is strongly dependent on frequency, a down chirp may also be used and may be more appropriate in some instances. Furthermore, it may also be appropriate to transmit high frequencies at a higher voltage level.

For imaging purposes, a chirp must be converted into a pulse before detection and display. This is accomplished by way of the matched filter 320. A matched filter is a filter whose frequency response is the complex conjugate of the frequency spectrum of a signal to be "matched." By shifting the frequency of the incoming linear FM chirp, the output pulse of the matched filter will vary in the time that it exits filter 320 (and 720 at FIG. 11). This delay, is directly proportional to the shift of the chirp signal away from its original center frequency. Thus, with an appropriately designed matched filter, variable time delays can be implemented via frequency shifts.

Using chirps (or other suitable coded signals), the frequency of every row and column signal is chosen such that the resulting shift in frequency will give rise to the appropriate time delay once the chirp is compressed into a pulse by a matched filter.

Composite and Non-Linear Implementations

The array 100 has at least two implementations. A first is the composite implementation where essentially all the components of each cell are fabricated in semiconductor material and the electro-acoustic transducer is connected thereto. A second implementation involves selecting an appropriate non-linear electro-acoustic, non-linear dielectric material (discussed immediately below) that performs the necessary mixing functions of one or both of the first and second mixers as a characteristic property thereof. With respect to the depiction of array 100 in FIG. 2, it should be recognized that the symbols for the first and second mixers represent, in the first implementation, physical mixers, and in the second implementation, functions that are being performed by the non-linear electro-acoustic, non-linear dielectric material. In addition, in the second implementation, the other electronic components, i.e., the buffer, T/R switch and amplifiers are not provided in the physical array, but amplifiers and the like are provided off board.

One reason for pursuing the non-linear implementation is that it is more cost effective. The quadratic relationship of the applied voltage to mechanical strain of an electrostrictive transducer can be used to mix the row and column control signals. Such an array can be constructed with rows of electrodes connected to one face of all the transducers and columns of electrodes connected to the other face (i.e., back). In a preferred embodiment, the non-linear electro-acoustic, non-linear dielectric material is electrostrictive with a dielectric constant that changes with applied electric field. Furthermore, barium strontium titanate is preferred.

In operation, the voltage at each array element will be the sum of the signal on its face and back. The resulting strain will be the square of this sum. With the appropriate choice of front and back control signal frequencies (row and column), only the sum (or difference) frequency and phase component will fall within the pass-band of the transducer and be radiated.

Electrostrictive transducers can also be used in receive providing that the transducer material has a large non-linear dielectric response as well as a large electrostrictive response. The required row and column mixing is performed by the non-linear dielectric response. In other words, an electric field is produced that is, for example, the square or some other non-linear response of the electric field across the transducer due to the non-linear dielectric response of the transducer material. In receive, the effect of electrostriction is to change the dielectric constant (permittivity) of the transducer as a function of mechanical stress resulting from the incoming acoustic field. Parametric mixing takes place between the electric and acoustic fields to produce an electro-acoustic signal. This produces a number of frequency components (at least 4) only one of which will be the desired signal. Through a suitable choice of materials and control frequencies such operation can, create the desired 2-D focus of acoustic energy.

Referring now to the composite implementation, this implementation provides several advantages, mostly stemming from its manufacture in semiconductor material that permits the incorporation of a large range of electronic circuits. Some of the advantages of the composite implementation are discussed herein. Also included is the possibility to integrate the row and column control circuits 30,40 on the array chip. Such integration would reduce the number of array connections from several hundred to a few dozen and significantly reduce the cost of the system. Integrating the array and the control circuits on a single chip also permits manufacture of a portable imaging system low enough in cost to be used in essentially all situations where volummetric and/or real time 2-D imaging are required.

OPERATION

All phased array imaging systems image by electronically synthesizing a lens. For 3-D imaging, one needs to synthesize a 2-D lens. In this case, the requisite delay over the aperture can be separated into two components, one that depends only on X and one that depends only on Y as taught herein.

For apertures that are less than one half the focal length (this is the normal operating condition for medical imaging), the lens equation can be approximated by a function that is separable into independent X and Y components. As seen in Equation 1, this is the classical paraxial approximation; an approximation that is the foundation for Fourier Optics as well as other field in wave mechanics.

$$\Delta(X,Y)=(X^2/(2*R)+Y^2/(2*R)/V \qquad \text{Eq. 1}$$

The paraxial approximation allows one to decompose a 2-D lens into two, orthogonal, 1-D lenses, one immediately in front of the other. At each point on the aperture, the phase delay from one lens adds to that of the other to produce the same phase delay as would result from a single 2-D lens. This means that a 2-D array can be used to synthesize a 2-D lens by phasing the rows with a phase relationship that will create a 1-D focus in the X-axis and the columns with one that will create a 1-D focus in the Y-axis. Such phasing is now discussed in more detail, first in a general continuous wave context and then in a context for broadband operation using coded signals.

In general operation, the row signals are used to produce a 1-D focus in the X direction while the columns signals are used to produce a 1-D focus along the Y axis. To achieve the desired 2-D focus, the row and column signals are combined in a manner such as that achieved by mixing (or multiplying) the signals together. Such mixing allows one to synthesize a 2-D focus using only as many control signals are there are rows and columns in array 100. In other words, this permits the effective control of M×N transducers by M+N control signals. Thus, the exemplary 10,000 transducers in array 100 (with M=N=100) can be controlled by 200 processing channels.

FIG. 2 shows several cells and transducers of the active 2-D array 100. Here each array element is connected to the output of its own electronic mixing circuit. One input of [the] each mixer is connected to an electrode that is shared by all other array elements on a given row. Likewise, the other input is connected to the corresponding column electrode. Mixing the external row and column signals together produces two signal components at each array element, one that is the sum of the frequency and phase of the row signal and the column signal, and the other which is the difference. By choosing the frequency of the row and column signals such that only the difference (or sum) frequency is within the pass-band of the transducer ensures that only the difference (or sum) frequency (and phase) component will be radiated from the array.

In receive, the desired 2-D control signal is created in the first mixer from the external row and column control signals. This signal, in turn, is mixed with the received signal from the transducer. The resultant signal is added to all others of the array elements of the composite structure. If, as shown, the output of the first mixer is not filtered, the output of the second mixer will contain four frequency components, only one of which is the desired signal. If desired, filters may be added in the composite implementation after each mixer. Though this will improve performance, a trade-off exists as to whether the increased performance is sufficient to justify the added expense and complexity of adding these devices. In the embodiment of FIG. 2, the desired component is preferably filtered by band pass filter 310 after summation. In the embodiment for sector scanning and discrete dynamic focusing (FIG. 11, etc.), filters are preferably provided after each mixer to eliminate extra frequency components.

Together with array 100, control signal generators 30, 40 comprise the beamforming process of system 10. The frequency and phase of the row and column array control signals determine the focus and angle of the transmit and receive beams in accordance with the equations herein. Having generally introduced transmit and receive operations, broadband applications [is] *are* now discussed.

Current imaging systems achieve sub-millimeter resolution by using short, high bandwidth pulses of acoustic energy. This same level of high bandwidth operation cannot be achieved in the M+N control line array 100 of FIG. 2 using continuous wave signals. Accordingly, a coded signal or the like, such as the linear FM chirp, is used to achieve high bandwidth and to thereby provide improved range resolution.

In transmit, the control signals are linear FM chirps having half the chirp rate of the transmitted acoustic signal (when they are mixed, the chirp rates add to produce a full chirp rate). The length of the chirps are also longer, in time, than the acoustic signal. The length of each control signal chirp depends upon the transmitted chirp length and the required delay for a particular focal point.

At each array element, the row signal and column signal are mixed together to produce several signals, one of which is a chirp that is the sum of the two control signals. By suitable choice of the base frequency of the control signals, the desired chirp component will be within the bandwidth of the acoustic transducer while the other components will fall significantly outside of this band. It should be recognized that this chirp component lasts much longer in time than the desired transmitted signal as well as covering a frequency range longer than the response of the transducer. The bandwidth of the transducer and the chirp rate is chosen such that the acoustic chirp transmitted from the element will be the desired length.

Referring to Equation 2, the relative timing of the transmit control signal at some array element is determined by the relative time of transit from a specific array element (a particular row-column, X-Y location) and the desired focal point (X,Y,θ,Φ,R). X and Y are the spatial location of the element, θ and Φ are the azimuth and elevation direction cosines of the ray connecting the center of the array to the focal point, and R is the range from the center of the array to the focal point. Using the paraxial approximation this simplifies to Equation 3.

Separating Equation 3 into X and Y components produces the row and column control signals. Equations 4 and 5 respectively, for transmit. In these equations, ωr and ωc are the row and column base frequencies. α is the chirp rate and V is the velocity of sound.

$$\Delta(X,Y)=\mathrm{sqrt}(R^2+X^2+Y^2-2XR\theta-2YR\Phi)/V-R/V \qquad \text{Eq. 2}$$

$$\Delta(X,Y)\cong(X^2/2R+Y^2/2R-X\theta-Y\phi)/V \qquad \text{Eq. 3}$$

$$\cong\Delta(X)+\Delta(Y)$$

$$Sr(X)=\cos(\omega r*(t-\Delta(X))+\alpha*r^2/2-2\alpha*\Delta(X)*t+\alpha*\Delta(X)^2) \qquad \text{Eq. 4}$$

$$Sc(Y)=\cos(\omega c*(t-\Delta(Y))+\alpha*r^2/2-2\alpha*\Delta(Y)*t+\alpha*\Delta(Y)^2) \qquad \text{Eq. 4}$$

In receive, the purpose of the control signals which have the characteristics of continuous wave signals, is to shift the frequency and phase of each signal so that, as that signal occurs, it coherently adds with all the other signals as they progress in their time sequence. The net result is, for a single point source, a single output chirp whose length in time and frequency corresponds to the total time over which the acoustic energy is insonifing the array aperture. For a point source located at a large angle away from array 100, the resulting output chirp can last over 20 microseconds even though the chirp coming from the point source or target lasted only 10 microseconds.

Mathematically, this requirement to achieve coherence can be established by changing the phase and amplitude of every chirp so that the summed output produces a single chirp centered in time with the chirp signal arriving at the center element of the array. Equation 6 provides the condition for coherence (ωa is the base frequency of the received chirp). Solving for the frequency shift 'ωs*t', and the phase shift 'ψ', gives the frequency and phase shift for each array element to ensure a coherent sum, Equation 7. Separating this equation into its row and column components gives rise to the row and column control signals, Equations 8 and 9 respectively, for receive (ωlor and ωloc are the rows and column local oscillator frequencies and tz is the transit time from the center of the array 100 to the target).

$$\cos(\omega a*(t-tz)+\alpha*(t-tz)^2)=\cos(\omega\Delta*(t-\Delta(X,Y))+\alpha*(t-\Delta(X,Y))^2+\omega r*t+\psi) \quad \text{Eq. 6}$$

$$\omega s=2*\alpha*\Delta(X,Y)$$

$$\psi=\omega a*\Delta(X,Y)-\alpha*(\Delta(X,Y))^2 \quad \text{Eq. 7}$$

$$Sr=\cos(\omega lor*t+2*\alpha*\Delta(X)*t+\omega a*\Delta(X)-\alpha*(\Delta(X)^2)) \quad \text{Eq. 8}$$

$$Sc=\cos(\omega loc*t+2*\alpha*\Delta(Y)*t+\omega a*\Delta(Y)-\alpha*(\Delta(Y)^2)) \quad \text{Eq. 9}$$

Dynamic Focusing

In current pulsed array imaging systems, a single pulse of acoustic energy is transmitted from an array for every line of range data that is collected. As that pulse travels away from the aperture it interacts with progressively deeper objects (targets). For best resolution, the focal length of the system is dynamically changed to follow the pulse as it interacts with objects at ever increasing ranges. This process is known as dynamic focusing and is one of the main advantages of array technology. Furthermore, dynamic focusing and discrete dynamic focusing, discussed below for sector scanning, permit the generation of real time images.

For linear or curved linear scanning or planar or curved planar scanning as taught herein, the direction cosines are zero. Without correction, the response of the system will fall away from the chosen focal range. To correct for this problem, the control signals must change in time in such a way as to keep all points in range in focus as they are sequentially insonified by the transmit chirp. Since the acoustic energy must travel from the array to some target and back again, the effective rate at which the targets are insonified is ½ the speed of sound. Thus to keep targets at different ranges in focus, the system must increase its focal distance at ½ the speed of sound.

Due to the time dependence of the focal changes, simply substituting R=½*V*t into the control signals gives rise to a DC signal and is not adequate. Appropriate delay, δ(t), is determined by the frequency of the control signals, Equation 10. The phase evolution of the control signals can be found by integrating this frequency shift, ωs(t), as demonstrated in Equations 11 and 12. To determine the constants of integration, some time 'Tm' is chosen to be the beginning point of the dynamic focusing process. The constant of integration is found by setting equations equal to Equations 11 and 12 at the time Tm. The result, for dynamic focusing is the control signals described by Equations 13 and 14.

$$\delta(t)=\omega s/(2*a)$$

$$\omega s(t)=2*a*(X^2/(V*t)+Y^2/(V*t)) \quad \text{Eq. 10}$$

$$\begin{aligned}\text{Phase}(x) &= \text{integral}(2*\alpha*\Delta(X,t)dt) \\ &= 2*\alpha*X^2*\text{in}(t)+K1\end{aligned} \quad \text{Eq. 11}$$

$$\begin{aligned}\text{Phase}(y) &= \text{integral}(2*\alpha*\Delta(Y,t)dt) \\ &= 2*\alpha*Y^2*\text{in}(t)+K2\end{aligned} \quad \text{Eq. 12}$$

$$Sr=\cos(\omega lor*t-2*\alpha*X^2*\text{In}(t/Tm)+2*\alpha*\Delta(X,Tm)+\omega a*\Delta(X,Tm)-\alpha*\Delta(X,Tm)^2) \quad \text{Eq. 13}$$

$$Sc=\cos(\omega lor*t-2*\alpha*Y^2*\text{In}(t/Tm)+2*\alpha*\Delta(Y,Tm)+\omega a*\Delta(Y,Tm)-\alpha*\Delta(X,Tm)^2) \quad \text{Eq. 14}$$

It should be noted that at scan angles more than a few degree, continuous dynamic focusing is not possible. This is due to the 2XRθ and 2YRΦ terms in Equation 2. The rate of change in the focal length causes these terms to introduce a frequency shift that significantly degrades the output signal.

Planar Array

Figure 5:
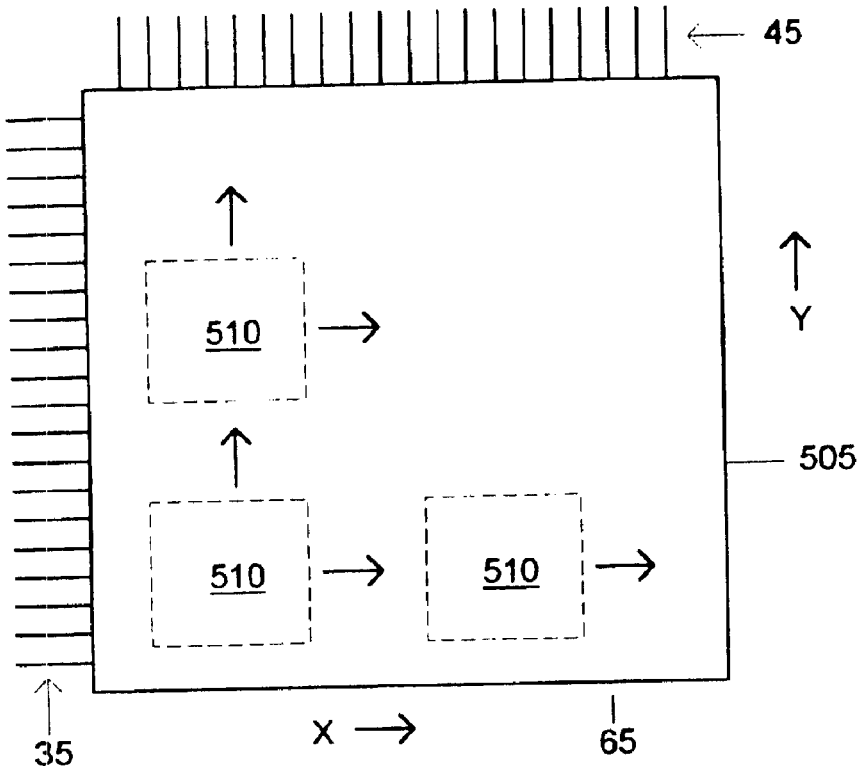
FIG. 5 is a diagram of planar scanning in accordance with the present invention.

Referring to FIG. 5, a diagram of a planar array 505 in accordance with the present invention is shown.

Row control lines 35 and column control lines 45 are connected to the planar array 505 to deliver the appropriate control signals discussed herein and the collective output signal from transducers (not shown) in array 505 is propagated on line 65 to the interface circuit 20.

Planar scanning is achieved by setting the direction cosines to zero in Eq. 2 and electrically translating a sub-aperture 510 across the array 505. Electrically translating a sub-aperture is generally known and its implementation in system 10 would be apparent to one skilled in the art given the teachings herein. Similar scanning in either an X or Y direction in 1-D arrays has been termed "linear" scanning. The term "planar" scanning is used herein to denote scanning a sub-aperture in both the X and Y directions in a 2-D array. Though the array 505 and sub-aperture 510 may have any practical dimension, in one practical embodiment the X and Y dimensions of the array 505 are approximately each 4" and the dimensions of the X and Y sub-aperture 510 are approximately each ¾".

Curved Planar Array

Referring to FIG. 6a, a convex curved planar array 550 and a less 555 therefor in accordance with the present invention are shown. The control lines and processing circuitry (not shown) for the array 550 are as taught herein.

Providing that the curved planar array 550 is not excessively curved relative to its active sub-aperture, for example for a sub-aperture of 1.5 cm a curved planar array with a curvature of r=4 cm is suitable, dynamic focusing can be achieved at a large angle by electronically translating a sub-aperture over array 550. Electrically translating a sub-aperture across a curved array is generally known. By the curvature of the array 550, the sub-aperture is able to scan an angle with the direction cosines equal to zero.

The less 555 provides focal point adjustment. For example, without the acoustic lens 550, an electronic focal length of 3 cm would correspond to an acoustic length of 6 cm due to a 4 cm convex curvature of array 550. Using a lens 550 having an acoustic velocity 0.8 that of water, the acoustic focal length is reduce to 4 cm. The convex shape of array 550 acts as a diverging lens. The acoustically slow convex covering 550 acts as a diverging lens that removes some of the diverging curvature of the wavefront. The array curvature has a significantly less pronounced affect at a 9 cm focal length. It should be recognized that although a diverging lens 555 is shown, a converging lens or no lens at all may be utilized.

Referring to FIG. 6b, a concave curved planar array 570 in accordance with the present invention is shown. An acoustic lens 575 is also provided for focusing acoustic energy from array 570.

Curved planar scanning can be achieved in both the composite and non-linear implementations.

Sector Scanning

As noted above, continuous dynamic focusing is achievable when angular or sector scanning is not performed. Discontinuous or discrete focusing however, can be achieved in angular scanning systems at a level that approximates continuous focusing if additional electronic componentry (discussed below) is added to system 10. The additional electronic componentry is implemented in the semiconductor material of the composite implementation, but the functions it provides are not properties of non-linear electro-acoustic material. Accordingly, sector scanning can be achieved only in the composite implementation.

Sector scanning requires that the transmit and receive beams be scanned over a predefined angle, normally +/−45 degrees (direction cosines +/−0.5 and +/−0.5, azimuth and elevation, i.e., X and Y). Increasing the pointing angle to 45 degrees in both azimuth and elevation significantly degrades the response. To correct for this distortion, an additional cross term is required and it is:

$$Err=(X*Y(\theta*\Phi)/(R*V) \quad \text{Eq. 16}$$

As this term contains information unique to the X and Y position of a given, it cannot be incorporated into row and column control signals. This is why the non-linear array is not effective at large angles.

Figure 7:
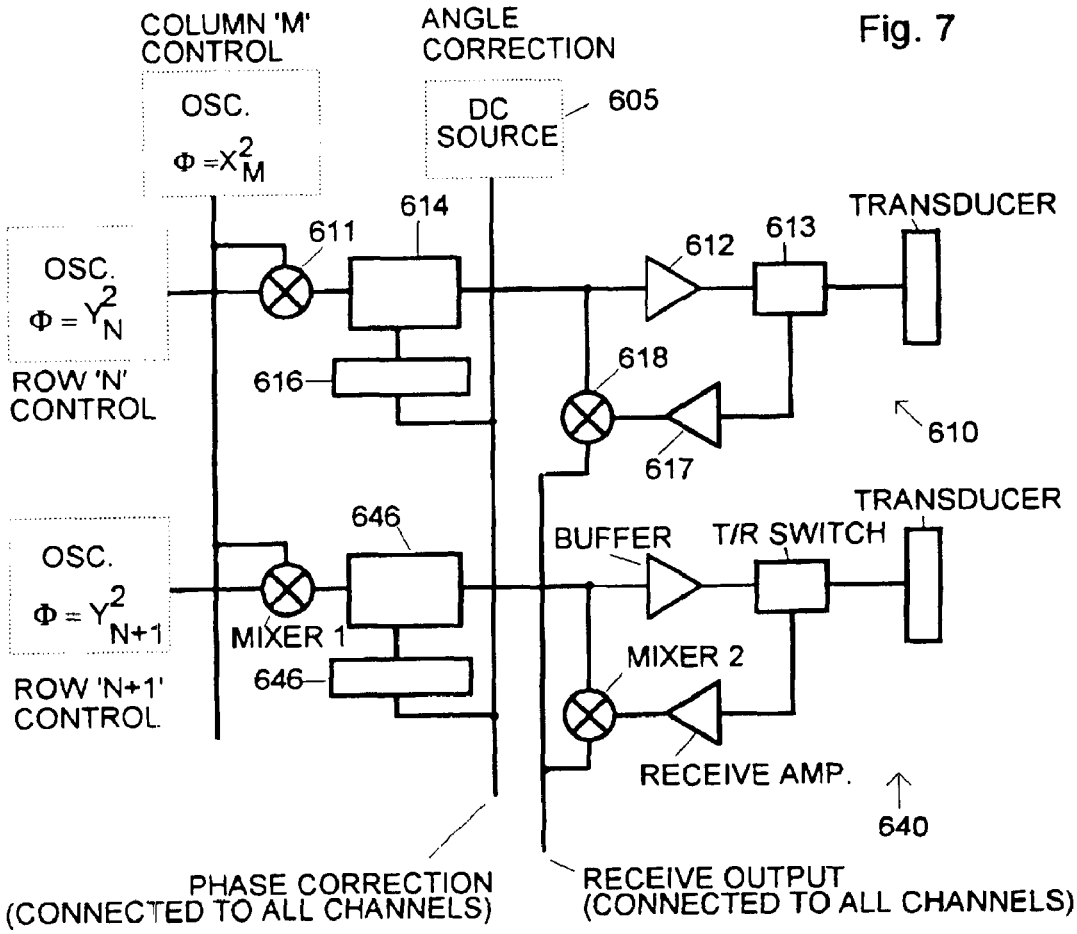
FIG. 7 is a schematic diagram of two cells of FIG. 2 with phase adjustment in accordance with the present invention.

Referring to FIG. 7, a schematic diagram of two transducer cells with phase adjustment for angular scanning in accordance with present invention is shown. The two cells 610 and 640 are analogous to cells 110 and 140, for example, of FIG. 2.

Referring to cell 610, the first mixer 611, buffer 612, T/R switch 613, amplifier 617 and second mixer 618 are analogous to their counterparts in cell 110. Cells 610, 640 each include a phase shifter 614, 644 and a voltage divider 616, 646. A DC signal source 605 for generating a common DC control signal is connected to the voltage divider. It is controlled by an additional processing channel (not shown).

The limitations imposed by Eq. 15 are removed by the addition of the phase shifters 614, 644 as programmed by the voltage divider outputs. The voltage dividers 616, 646 essentially comprise two resistors that can be precisely selected to divide the common DC signal to a unique voltage level. This voltage level or ratio of input to output voltage is chosen for each cell to be proportional to its XY position in the array (100 of FIG. 2). Eq. 16 shows the relationship of the DC control signal and Eq. 17 shows the actual phase shift introduced by each phase shifter in array 100 (FIG. 2), represented in FIG. 7 by phase shifters 614 and 644.

$$Scorr=(\theta+\Phi)*(\omega a+2*a*R/V)/(2*R*V) \quad \text{Eq. 16}$$

$$C=X*Y*Scorr \quad \text{Eq. 17}$$

The immediately preceding discussion illustrated a way of achieving unique phase correction for each transducer for achieving angular scan in transmit. A way of angularly focusing in receive is now discussed.

Prior art acoustic imaging systems sample the output image at discrete ranges. For this reason, a continuous output, in range, is not required. One can use a sequence of range outputs, in other words, discontinuous or discrete dynamic focusing, without any loss in image quality that is detectable by the human eye.

Figure 8:
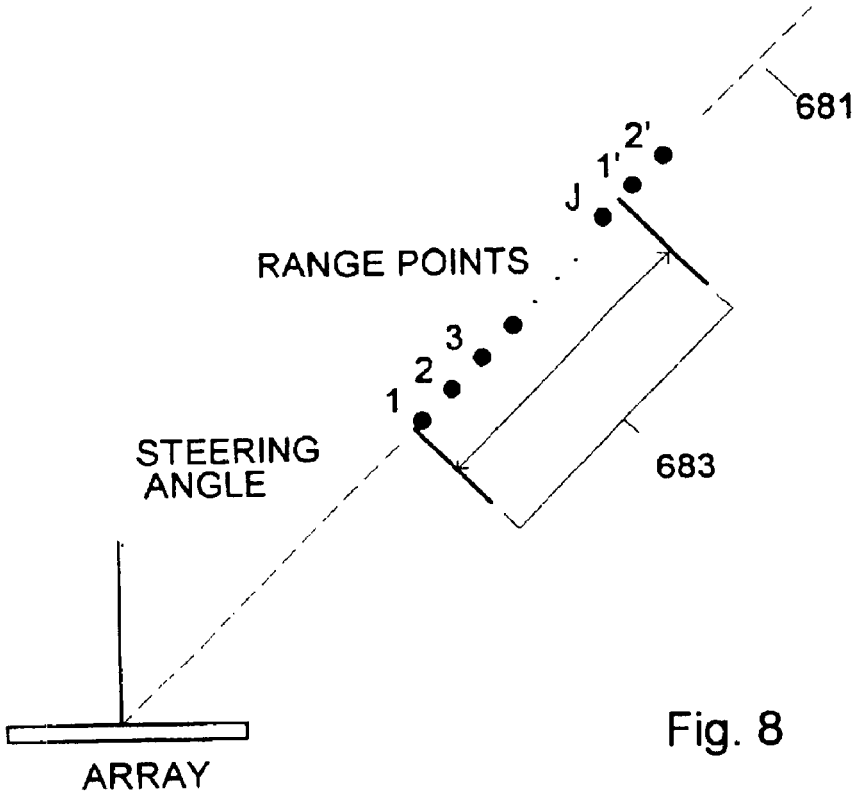
FIG. 8 is a diagram illustrating aspects of discrete dynamic focusing in accordance with the present invention.

In the composite implementation, discrete focusing is achieved by at least the two following approaches or a combination thereof. A first approach is to use as many processing electronic cells per transducer as the number of range increments desired. The control signals only have to be in existence for the duration over which the energy from a particular range point insonifies the array. This concept is illustrated in FIG. 8, wherein dashed line 681 represents a ray or line emanating from the center of array 100 on which range points for focusing lie. The ray 681 is defined by certain elevation and azimuth angles. Segment 683 represents one process period which is essentially the time over which energy from a focused range point insonifies the array. The range focus along ray 681 is sequential extended a distance equal to the speed of sound in the relevant medium times the period of insonification, up to a distance that is no longer practical or desirable for scanning. For a practical design for use in medical ultrasound imaging, the process period is on the order of 20 microseconds. This means that every 20 microseconds, the control signals can change to focus on a new range point. Having 40 processing cells for every array element would permit one range sample every 0.5 microseconds; approximately what is used for current imaging systems when displaying 16 cm of range.

A second approach to obtain multiple range samples is to use the high electronic bandwiths of current integrated electronic circuits. Assuming a bandwidth requirement of 10 MHz per range channel, a 400 MHz electronic bandwidth would permit 40 simultaneous range channels. Implementation of this approach in the imaging system 10 described herein is now presented.

Referring to FIG. 9, a range versus frequency band diagram for implementing discrete focusing is shown. A plurality of range points are defined, point 1, point 2, . . . point j, that sufficiently approximate the range overwhich focusing is desired along a particular ray (681 of FIG. 8). A specific frequency band, band 1, band 2, . . . band j, is defined for each range point.

Referring to FIG. 10, a phase accumulator 691 is provided either in or in communication with the interface circuit 20. The phase accumulator 691 preferably receives a digital signal, ν(t), from signal generating circuitry (not shown, but generally known), in system control circuitry that includes components for each of the j frequency bands of FIG. 9. Thus, $$\nu(t)=\nu(t)_2'+\nu(t)_2'+\ldots+\nu(t)_j' \quad \text{Eq. 19}$$

where $\omega lor_1+\omega loc_1$=band $\nu(t)_1$ center frequency and $\omega lor_2+\omega loc_2$=band $\nu(t)_2$ center frequency, etc.

The phase accumulator 691 preferably includes a digital to analog converter (not shown) or one is placed downstream thereof. The output of accumulator 691 is the Scorr signal which is delivered to the voltage dividers (616,646 of FIG. 7). The output of each voltage divider is the control signal, C, which is propagated to the phase shifters (614, 644 of FIG. 7) to uniquely code the receive focusing signal for each cell. In the exemplary embodiment, mentioned immediately above, each band or frequency component ν(t)' differs by 10 MHz from the adjacent band. Thus, for 40 range channels, ν(t) has a band width of 40×10 MHz=400 MHz.

Figure 11:
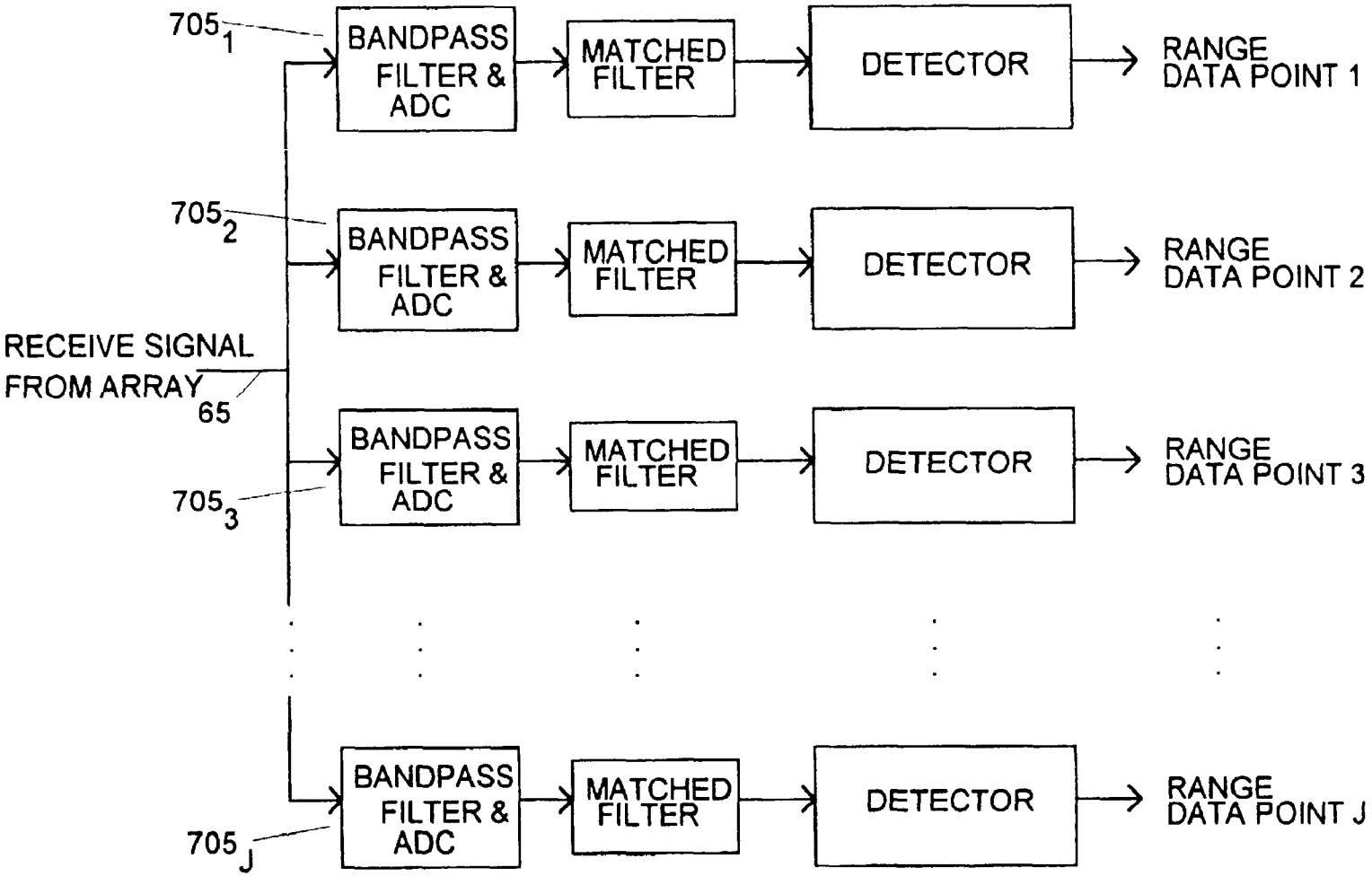
FIG. 11 is a block diagram of a modified receive channel in accordance with the present invention.

Referring to FIG. 11, a modification in the interface circuit 20 to appropriately process a multi frequency component signal in accordance with the present invention is shown.

In contrast to the singular receive channel 305 of the embodiment of FIG. 3, the embodiment of FIG. 11 includes j receive channels 705 (705$_1$, 705$_2$, 705$_j$) which contain matched filters 720$_1$, 720$_2$, 720$_j$ that are specifically configured for their corresponding frequency component $\nu(t)_1'$, $\nu(t)_2'$, $\nu(t)_j'$, respectively. Continuing with the current example of 40 range points and 40 frequency components, there are 40 receive channels 705 in the modification to the interface circuit 20 illustrated in FIG. 11. It should be recognized that one can combine multiple cells per transducer, for example 6 cells per transducer (with appropriate frequency multiplexing and phase shifting as taught herein), with larger bandwidth signals, for example 6 frequencies in the bandwidth and 6 receive channels, to achieve the desired number of range samples, in this example, 6×6=36.

1-D Implementation and Annular Array

Figure 12:
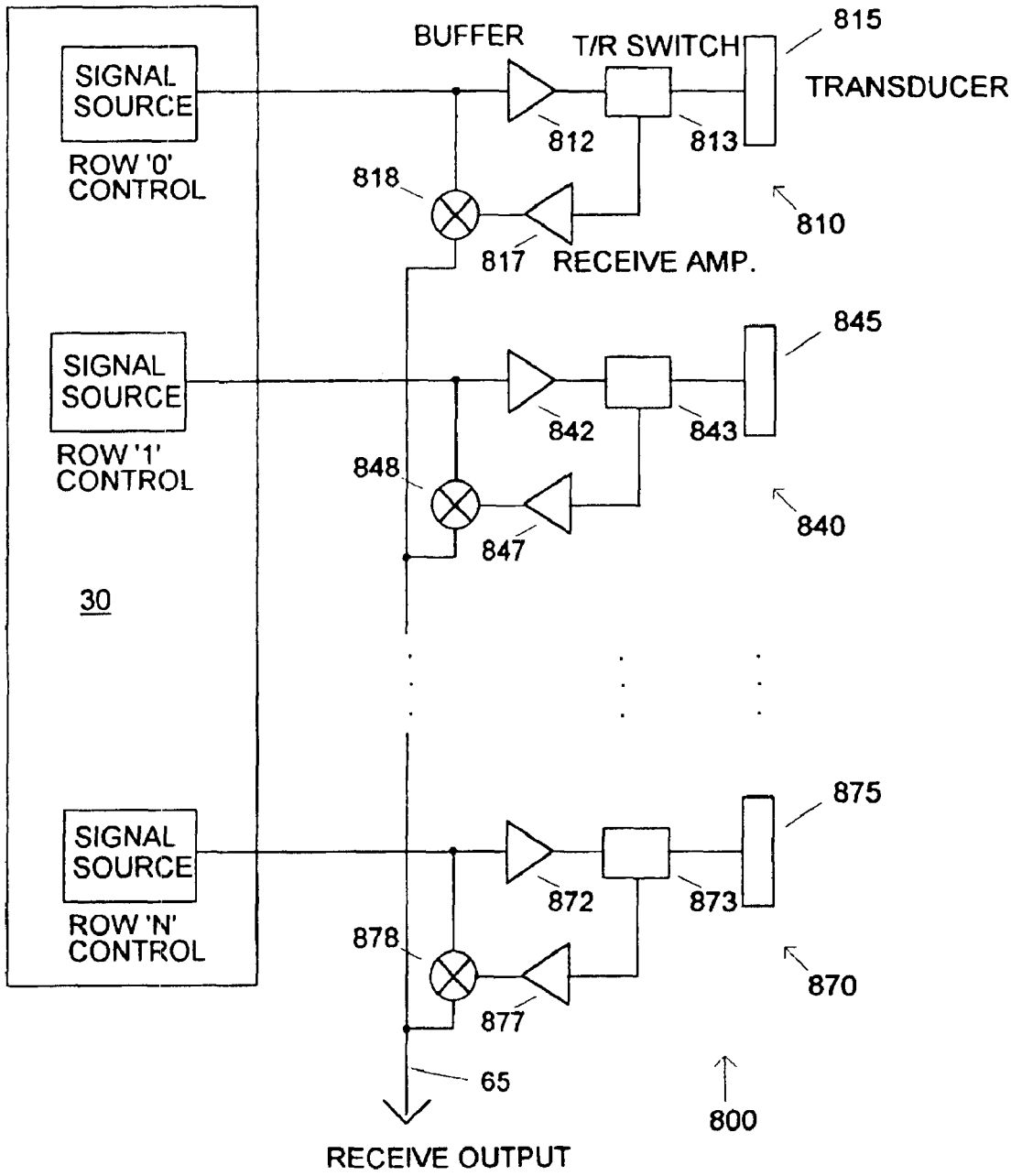
FIG. 12 is a schematic/block diagram of an embodiment of a 1-D array in accordance with the present invention.

Referring to FIG. 12, a 1-D array 800 for an acoustic scanning system in accordance with the present invention is shown. The array 800 is integrated into the system 10 of FIG. 1, replacing array 100. Since array 800 is one dimensional, control lines are only implemented in one dimension, either row or column control. The row control circuiting 30 is shown in FIG. 12 and hence in integrating array 800 into system 10, the column circuit 40 and related electronics are removed. Each cell 810,840,870 does not contain a first mixer, such as mixer 111 and the like of FIG. 2 because of the absence of column control lines, but does include a buffer 812,842,872, a T/R switch 813,843, 873 receive amplifier 817,847,877 and a second mixer 818, 848, 878. Each cell is connected to a transducer 815,845, 875. Cells 810,840,870 are otherwise generally analogous to cells 110,140,170 of FIG. 2. Accordingly, they may be implemented as a composite array or non-linear array and be configured in embodiments for linear and curved linear scanning in both implementations, and for sector scanning in the composite implementation. In addition, the 1-D array can be implemented as a discrete array coupled to discrete electronics. The 1-D array 800 operates under the same signal generating and processing aspects taught herein, with the exception of those aspects specific to the mixing of row and column signals.

It should also be recognized herein that the teachings herein apply to annular arrays and they could, accordingly, be fabricated in the same embodiments of a 1-D array discussed immediately above.

Aberration Correction

The various tissues of the body have differing speeds of sound. Not correcting the beamforming process for this fact may degrade the acuity of the resulting acoustic images. To date, modest improvement in image quality has been achieved by aberration correction techniques on 1-D phased arrays. It is generally accepted, however, that these methods would produce a significant increase in image quality if they could be applied to large 2-D apertures. Thus, perhaps the most significant impediment to aberration correction has been the expense and complexity of building a 2-D array imaging system.

Use of the present invention makes practical a 2-D scanning system and hence makes possible aberration correction techniques. The required delay perturbations are achieved by suitable modification of the row and column control signals. In a relatively basal embodiment, the system can implement any delay profile that is separable into X and Y components. Since the present system has been shown to correct the large first and second order delays required to produce an image in homogeneous media, the constraints of separability upon the improvement in image quality and general system performance should not be significant.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

I claim:

1. An acoustic imaging apparatus, comprising:

control logic;

a plurality of transducer elements arranged in an array, each coupled to said control logic and capable of transmitting an acoustic signal representative of an electrical transmit control signal propagated from said control logic and generating an electrical receive signal representative of an incident acoustic signal;

means within said control logic for generating an electrical transmit control signal for each transducer element such that the electrical transmit control signal for each transducer element contains a coded signal;

means within said control logic for generating an electrical receive control signal for each transducer element such that the electrical receive control signal for each transducer element contains a frequency and phase shift than when combined with the transducer element's electrical receive signal modifies the frequency and phase of that electrical receive signal in such a manner as to permit the coherent combination of the modified electrical receive signals from all of said plurality of transducer elements;

means for combining the electrical receive control signal of each transducer element with an electrical receive signal generated by that transducer;

means coupled to each of said transducer elements for combining the modified electrical receive signals from said transducer elements so as to form a coherently combined array output signal;

means coupled to said transducer output combining means for decoding a combined reflected coded signal in the coherently combined array output signal to produce a decoding means output signal; and means coupled to said decoding means for generating image data from said decoding means output signal.

2. The apparatus of claim 1, *wherein* said coded signal is a chirp.

3. The apparatus of claim 2, wherein said decoding means comprises at least one matched filter for coded signal decoding.

4. The apparatus of claim 1, wherein said chirp is a linear FM chirp.

5. The apparatus of claim 1, wherein said array has a size of M rows and N columns and said electrical transmit control signal generating means comprises means for generating individual row and column transmit control signals for each of said rows and columns, the electrical transmit control signal for each transducer element being a combination of the transmit row and column control signals for that transducer.

6. The apparatus of claim 5, wherein at least one of said row and column transmit control signals for a given transducer element contains a frequency based coded signal.

7. The apparatus of claim 5, wherein said electrical receive control signal generating means comprises means for generating individual row and column receive control signals for each of said rows and columns, the electrical receive control signal for each transducer being a combination of the receive row and column control signals for that transducer.

8. The apparatus of claim 1, wherein said coded signal includes a frequency based code.

9. The apparatus of claim 1, wherein said array is a one dimensional array with a plurality of rows and one column.

10. The apparatus of claim 1, wherein said array of transducer elements comprises M rows and N columns, where M and N are positive integers and at least one of M and N is greater than 1;

at least one of said transmit control signal generating means and said receive control signal generating means includes means for generating row and column control signal components; and wherein each transducer element includes an active electronic device for combining said row and column control signal components for that transducer element.

11. The apparatus of claim 1, wherein each transducer element includes a transducer comprised of a non-linear electro-acoustic, non-linear dielectric material.

12. An acoustic imaging apparatus, comprising:

a plurality of electro-acoustic transducer elements arranged in an array, each capable of transmitting an acoustic signal and generating an electrical signal representative of an incident acoustic wave;

control means having a plurality of control channels coupled to each of said plurality of transducer elements, said control channels being fewer in number than said transducer elements;

wherein said control means generates control signals for each transducer element that when combined with the electrical receive signal of that transducer element modifies the electrical receive signal in such a manner as to permit the simultaneous processing of the modified electrical receive signals from said plurality of transducer elements;

means for combining the modified electrical receive signals of each of said transducer elements to form an array output signal; and means coupled to said combining means for generating image data from said array output signal.

13. The apparatus of claim 12, wherein said array has a plurality of rows and a plurality of columns each having one of said plurality of control channels associated therewith;

said control signal generating means further including means for generating row and column control signal components; and wherein said transducer element is uniquely and simultaneously controlled by a combination of the row and column control signal components for that transducer element.

14. The apparatus of claim 12, wherein said control signal generating means further includes means for generating a transmit control signal for each transducer element that contains a frequency based coded signal for transmission by each transducer element.

15. The apparatus of claim 14, further comprising means for decoding a reflected frequency based coded signal.

16. An acoustic imaging system, comprising:

an array of electro-acoustic transducer elements having M rows and N columns, where M and N are positive integers and at least one of M and N is greater than one;

M row control lines, each coupled to the transducer elements in one of said M rows;

N column control lines, each coupled to the transducer elements in one of said N columns;

control means coupled to each of said M row and N column control lines for generating row control signals for each of said row control lines and column control signals for each of said column control lines, a control signal for each transducer being a combination of one of said row control signals and one of said column control signals;

a plurality of active devices, each coupled to one of said transducer elements for combining the row control signal and the column control signal of that transducer element;

means for combining the output of each transducer element to produce an array output signal; and means coupled to said transducer output combining means for generating image data from said array output signal.

17. The apparatus of claim 16, wherein said active device is an active electronic device.

18. The apparatus of claim 17, wherein said control means includes means for generating a transmit control signal that contains a frequency based coded signal for each transducer element; and wherein said apparatus further comprises means in communication with each of said transducer elements for modifying a reflected coded signal received thereby to achieve a delay encoded in the coded signal, said delay for each transducer element being based on the relative position of that transducer element in the array.

19. The apparatus of claim 16, wherein said active device includes a non-linear electro-acoustic material.

20. The apparatus of claim 16, wherein said active device includes a non-linear electro-acoustic material for combining row and column control signal on transmit and an active electronic device for combining row and column control signal on receive.

21. The apparatus of claim 16, wherein said active device includes a non-linear electro-acoustic, nonlinear dielectric material.

22. A method for acoustic imaging, comprising the steps of:

providing control logic;

providing a plurality of transducer elements arranged in an array, each coupled to said control logic and capable of transmitting an acoustic signal representative of an electrical transmit control signal propagated from said control logic and generating an electrical receive signal representative of an incident acoustic signal;

generating an electrical transmit control signal for each transducer element such that the electrical transmit control signal for each transducer element contains a coded signal;

generating an electrical receive control signal for each transducer element that contains an appropriate frequency and phase shift that when combined with that transducer element's electrical receive signal permits the coherent combination of the electrical receive signals of each of the plurality of transducer elements;

combining the coherent output signals from said transducer elements so as to form a coherently combined array output signal;

decoding a combined reflected coded signal in the coherently combined array output signal to produce a decoded output signal; and generating image data from the decoded output signal.

23. An acoustic imaging apparatus, comprising:

control logic;

a plurality of transducer elements arranged in an array, each coupled to said control logic and capable of transmitting an acoustic signal representative of an electrical transmit control signal propagated from said control logic and generating an electrical receive signal representative of an incident acoustic signal;

means within said control logic for generating an electrical transmit control signal for each transducer element that contains a frequency based coded signal and [cause] *causing* each transducer to emit an acoustic signal representative of said coded signal;

means for modifying the frequency and [chase] *phase* of an electrical receive signal of each transducer element for coherently combining reflected coded signals within the electrical receive signals thereof;

means coupled to said modifying means for decoding the combined reflected coded signals to achieve a time delay based on that coded signal; and means coupled to said decoding means for generating image data from an output signal therefrom.

*24. An acoustic energy transmitting apparatus, comprising:*

*a plurality of electro-acoustic transducer elements arranged in an M row by N column array, where M and N are positive integers and at least one of M and N is greater than one;*

*control circuit for propagating row and column control signals for each of said M rows and said N columns, each control signal having a frequency and a phase component; and*

*wherein each transducer element is configured to function as an active device so as to achieve a combining at each transducer element of the frequency and phase components of the row and column control signals for that transducer element in such a manner as to provide a focused acoustic signal at a given focal distance and direction from said array.*

*25. The apparatus of claim 24, wherein the electric signal to acoustic signal relationship and vice versa of each transducer element is non-linear.*

*26. The apparatus of claim 24, wherein said control circuit includes a control channel for each of said M rows and a control channel for each of said N columns, and wherein the number of control channels is fewer than the number of transducer elements.*

*27. The apparatus of claim 24, wherein said control circuit is configured such that the row and column signals for at least some of the transducer elements includes a coded signal.*

*28. The apparatus of claim 27, wherein M equals one.*

*29. An acoustic energy transmitting apparatus, comprising:*

*a plurality of electro-acoustic transducer elements arranged in an M row by N column array, where M and N are positive integers and at least one of M and N is greater than one;*

*M row control lines, each coupled to the transducer elements in one of said M rows;*

*N column control lines, each coupled to the transducer elements in one of said N columns;*

*control circuit for propagating row and column control signals for each of said M rows and said N columns, a control signal for each transducer element being a combination of one of said row control signals and one of said column control signals;*

*a plurality of active devices, each coupled to one of said transducer elements for combining the row control signal and the column control signal of that transducer element;*

*wherein said transducer elements, control circuit and active devices are configured so as to achieve a combining at each transducer element of the row and column control signals for that transducer element in such a manner as to provide a focused acoustic signal at a given focal distance and direction from said array; and*

*wherein each of said electro-acoustic transducer elements is configured within said apparatus to function in a non-linear manner in operation.*

*30. An acoustic energy receiving apparatus, comprising:*

*a plurality of electro-acoustic transducer elements arranged in an M row by N column array;*

*control circuit for propagating row and column control signals for each of said M rows and said N columns, each row and column control signal having a frequency and a phase component; and*

*wherein said transducer elements and said control circuit are configured so as to achieve a combining at each transducer element of the frequency and phase components of the row and column control signals for that transducer element with a resultant electrical receive signal, corresponding to an acoustic signal incident on that transducer element, in such a manner as to modify the frequency and phase of the transducer element's electrical receive signal so as to achieve the coherent combination of the modified electrical receive signals from all of said plurality of transducer elements; and*

*a filter that filters spurious frequencies output from the transducer elements;*

*wherein said transducer elements, control circuit and filter are configured to achieve focused acoustic signal reception at a given distance and direction from said array.*

*31. The apparatus of claim 30, wherein said transducer elements and said control circuit are configured to achieve dynamic focused acoustic signal reception.*

*32. The apparatus of claim 31, wherein the electric signal to acoustic signal relationship and vice versa of each transducer element is non-linear.*

*33. The apparatus of claim 30, wherein said filter includes a matched filter.*

*34. The apparatus of claim 33, wherein said matched filter includes a conjugate of a coded signal.*

*35. The apparatus of claim 29, wherein M equals one.*

*36. The apparatus of claim 30, further comprising a circuit that generates image data from the coherent combination of transducer element receive signals.*

*37. The apparatus of claim 30, wherein said control circuit includes a control channel for each of said M rows and a control channel for each of said N columns, and wherein the number of control channels is fewer than the number of transducer elements.*

*38. An acoustic energy receiving apparatus, comprising:*

*a plurality of electro-acoustic transducer elements each capable of generating an electrical receive signal in response to an incident acoustic wave and arranged in an M row by N column array, where M and N are positive integers and at least one of M and N is greater than one;*

*control circuit for propagating row and column control signals for each of said M rows and said N columns, the control signal for each transducer element being a combination of the row and column control signals for that transducer element;*

*wherein said row and column control signals are configured, for each transducer element, such that when combined with the electrical receive signal of that transducer element the electrical receive signal is modified in such a manner as to permit the simultaneous processing of the modified electrical receive signals from said plurality of transducer elements;*

*a first circuit that combines the modified electrical receive signals of each of said transducer elements to form an array output signal; and*

*a second circuit coupled to said first circuit that generates image data from said array output signal.*

*39. The apparatus of claim 38, wherein M equals one.*

*40. The apparatus of claim 24, wherein each transducer element includes non-linear electro-acoustic material.*

* * * * *